United States Patent [19]
Roe

[11] Patent Number: 6,066,774
[45] Date of Patent: *May 23, 2000

[54] ABSORBENT ARTICLE WITH FIBER OPTIC WASTE INSPECTION SYSTEM

[75] Inventor: Donald Carroll Roe, West Chester, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/966,835

[22] Filed: Nov. 10, 1997

Related U.S. Application Data

[63] Continuation-in-part of application No. 08/931,676, Sep. 16, 1997, which is a continuation of application No. 08/688,387, Jul. 30, 1996, abandoned.

[51] Int. Cl.[7] ................................................ A61F 13/15
[52] U.S. Cl. ........................ 604/361; 604/358; 604/385.1; 604/385.2; 604/374; 604/365
[58] Field of Search ................................ 604/361, 358, 604/385.1, 374, 365, 385.2; 313/485; 23/230; 350/96.29; 156/227; 358/901.1

[56] References Cited

U.S. PATENT DOCUMENTS

| | | | |
|---|---|---|---|
| 2,127,538 | 9/1938 | Seiger | 128/138 |
| 3,759,261 | 9/1973 | Wang | 128/287 |
| 3,918,454 | 11/1975 | Korodi et al. | 128/287 |
| 3,952,746 | 4/1976 | Summers | 128/287 |
| 4,022,211 | 5/1977 | Timmons et al. | 128/287 |
| 4,637,078 | 1/1987 | Southwell | 2/408 |
| 4,796,014 | 1/1989 | Chia | 340/573 |
| 4,892,536 | 1/1990 | DesMarais et al. | 604/385.2 |
| 4,930,161 | 6/1990 | Cohen | 2/114 |
| 4,944,733 | 7/1990 | Casale | 604/385.1 |
| 4,955,876 | 9/1990 | Millner | 604/385.2 |
| 4,968,312 | 11/1990 | Khan | 604/388.1 |
| 5,062,840 | 11/1991 | Holt et al. | 604/385.1 |
| 5,078,708 | 1/1992 | Haque | 604/361 |
| 5,207,663 | 5/1993 | McQueen | 604/385.1 |
| 5,269,775 | 12/1993 | Freeland et al. | 604/385.2 |
| 5,304,159 | 4/1994 | Tanji et al. | 604/385.2 |
| 5,342,342 | 8/1994 | Kitaoka | 604/385.2 |
| 5,344,516 | 9/1994 | Tanji et al. | 156/164 |
| 5,354,289 | 10/1994 | Mitchell et al. | 604/361 |
| 5,364,381 | 11/1994 | Soga et al. | 604/366 |
| 5,383,867 | 1/1995 | Klinger | 604/385.1 |
| 5,417,680 | 5/1995 | Kimura et al. | 604/385.2 |
| 5,462,541 | 10/1995 | Bruemmer et al. | 604/391 |
| 5,568,128 | 10/1996 | Nair | 340/604 |
| 5,569,229 | 10/1996 | Rogers | 604/385.1 |
| 5,570,082 | 10/1996 | Mahgerefteh et al. | 340/604 |

FOREIGN PATENT DOCUMENTS

| | | | |
|---|---|---|---|
| 2033595 | 5/1992 | Canada | A61F 13/15 |
| 0 286 374 | 12/1998 | European Pat. Off. | A61B 5/00 |
| 802 243 | 2/1951 | Germany . | |
| 40 14 572 A1 | 11/1991 | Germany . | |
| 2 183 160 | 6/1997 | United Kingdom | A41B 13/02 |

*Primary Examiner*—John G. Weiss
*Assistant Examiner*—Miley C. Peppers, III
*Attorney, Agent, or Firm*—Thomas J. Osborne, Jr.; David M. Weirich; Steven W. Miller

[57] ABSTRACT

An absorbent article, such as a diaper, having a liquid permeable topsheet, a liquid impervious backsheet joined to the topsheet, an absorbent core located between a portion of the topsheet and the backsheet, and a fiber optic strand having two ends. The first end of the fiber optic strand is disposed in the crotch region of the absorbent article, and the second end is disposed adjacent to the backsheet of the absorbent article.

36 Claims, 9 Drawing Sheets

ABSORBENT ARTICLE WITH FIBER OPTIC WASTE INSPECTION SYSTEM

This is a continuation-in-part of application Ser. No. 08/931,676 filed on Sep. 16, 1997 which is a continuation of application Ser. No. 08/688,387 filed on Jul. 30, 1996 now abandoned.

TECHNICAL FIELD

The present invention relates to disposable, absorbent articles and, more particularly, to disposable, absorbent articles in which fiber optic material is provided in the article to enable a caretaker to selectively and easily determine whether the article is soiled.

BACKGROUND OF THE INVENTION

Today, disposable, absorbent articles, such as diapers and adult incontinence briefs, are widely used in infant and toddler care and in the care of incontinent adults, as a means of containing, isolating and disposing of bodily wastes. These articles have generally replaced reusable, washable cloth garments as the preferred means for these applications because of their convenience and reliability. The typical disposable article is a composite structure containing a number of layers of material. Included in these layers of material are generally a liquid impermeable outer layer or backsheet, one or more layers of material forming an absorbent core, and a liquid permeable inner layer or topsheet. The layers comprising the article are generally secured together by lines of adhesive, with the backsheet and topsheet usually directly adhesively interconnected around the periphery of the article. Elastic bands are often provided along the longitudinal sides of the article to constrict the topsheet and backsheet to produce leg cuffs, which fit snugly about the wearer's legs. In addition, closure devices, such as adhesive tabs, may be provided for removably fitting and holding the sides of the article together about the waist of the wearer. Alternatively, the article may be folded and sealed or otherwise attached along opposing side edges to form a pant or brief.

While many advancements have been made in the field of disposable articles for both infants and adults, which have enabled them to be widely preferred over conventional cloth garments, a number of problems still exist. Among the problems experienced with these disposable articles is the inability to determine whether the article has been soiled without substantially removing the article. It is desirable to detect soiling of the article as soon after it occurs as possible, in order to reduce the occurrence of diaper rashes and other skin irritations and infections.

Currently, there are a limited number of options available to a caretaker for determining whether an article, such as a diaper, has been soiled. The first of these options is to smell the article in order to detect the odor of stool or urine. While this option is non-intrusive to the wearer, it is highly subject to error, because the deodorants applied to the article may mask the odor of the waste and the odor of the waste may vary. Another option is for the caretaker to at least partially remove the article from the wearer to see whether it is soiled. While this method is more accurate, it is also more invasive and inconvenient, requiring at least a partial removal of the wearer's clothing and the absorbent article. A third option for inspecting the article is for the caretaker to stick a finger into the rear portion of the article to "feel" whether it is soiled. While this method also tends to be very accurate, it can be a rather inconvenient and/or unpleasant experience for at least the caretaker.

Articles have been developed which include transparent portions for viewing bodily waste in the article without the need for removing the article. For instance, Haque, U.S. Pat. No. 5,078,708, issued Jan. 7, 1992, discloses a diaper which includes a transparent outer layer and an opaque soft lining material. In the Haque diaper, openings in the form of character shapes are provided in both the front and back portions of the soft material, so that soilage can be readily viewed from outside the diaper. While the Haque diaper eliminates the need to remove the diaper to detect soilage, its transparent outer layer creates an unsanitary, unpleasant appearance, because the soilage is visible to not only the caretaker, but also to anyone else who is in visual contact with the wearer before the diaper is changed. Additionally, the viewing site must be at the location of the diaper where the soilage is present.

Accordingly, to overcome the above and other problems, it is desirable to have a disposable, absorbent article that includes fiber optic material to indicate when the article has been soiled without removing the article. In a preferred embodiment, the present invention also allows the indication to be provided at a remote location of the diaper away from the location of the soilage. Further, it is desirable to have such an article in which the sanitary outer appearance of the article is maintained.

SUMMARY OF THE INVENTION

The present invention is directed to an absorbent article having fiber optic material that indicates when the article has been soiled. Fiber optic materials provide the benefit of allowing the visual indicator to be placed either directly adjacent to the portion of the article that has been soiled or in one or more remote locations of the article. The transmission end of the fiber optic material is disposed in an area of the article where it will be in close proximity to the exudates discharged from the body such as adjacent to the topsheet or absorbent core. The reception end of the fiber optic material, however, may be disposed in any location where a change in the output from the reception end will provide a visual indication to the caretaker that the article has been soiled, such as adjacent to the backsheet. Thus, the reception end may be placed adjacent to the portion of the article that will be soiled or anywhere else on the article that will provide a visual indication that the article has been soiled. In a preferred embodiment of the invention, the reception end of the fiber optic material is disposed adjacent to the backsheet in the rear waist region so that the caretaker may visually inspect the indicator at the wearer's waistline without having to remove an extra article of clothing such as pants, shorts, etc.

In accordance with the purposes and advantages of the present invention as described above, an absorbent article, such as a diaper, is provided comprising a liquid permeable topsheet, a liquid impervious backsheet joined to the topsheet, an absorbent core located between at least a portion of the topsheet and the backsheet, and a fiber optic material having two ends. The first end of the fiber optic material is disposed in the crotch region of the absorbent article, and the second end is disposed adjacent to the backsheet of the absorbent article.

In another embodiment of the present invention, the disposable, absorbent article has a transparent or translucent inspection porthole at the reception end of the fiber optic material that may further include a releasably affixed cover for concealing the inspection porthole when it is not in use. In a further aspect of the present invention, the cover is at least partially detachable and is pliable so as not to detract from the wearer's comfort. In this embodiment, the cover is also preferably reclosable to allow for multiple inspections of the same article.

Additional objects, advantages and other novel features of the invention will be set forth in part in the description that follows and, in part, will become apparent to those skilled in the art upon examination of the invention. The objects and advantages of the invention may be realized and obtained by means of the instrumentalities and combinations particularly pointed out in the appended claims.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
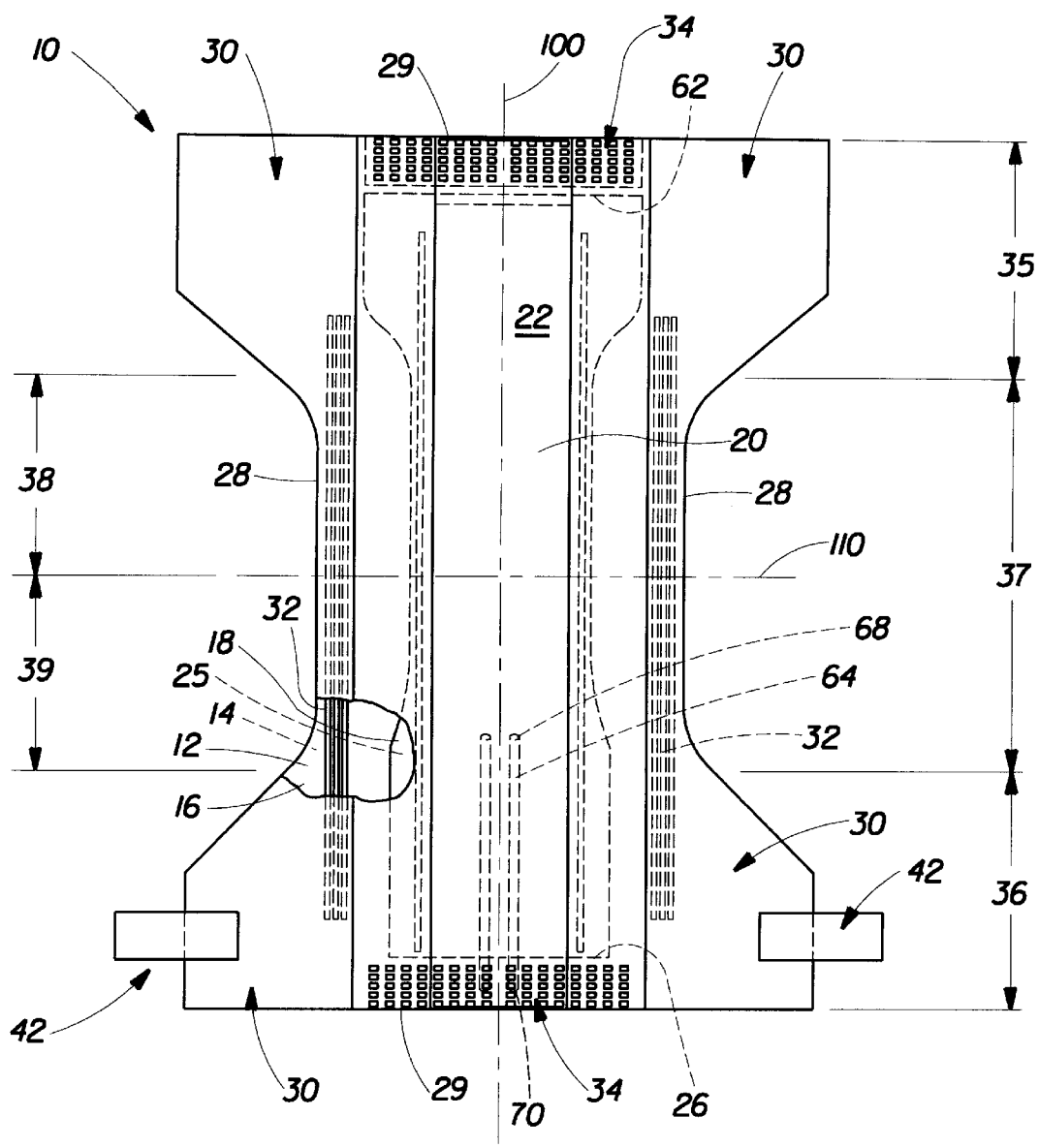
FIG. 1 is a plan view of an article made in accordance with the present invention in a flat-out state with portions of the structure being cut-away to more clearly show the construction of the article, wherein the article is a diaper.

Referring now to the drawings in detail, FIGS. 1–10 depict representative embodiments of an absorbent article made in accordance with the present invention, wherein the article is a disposable diaper. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention, which is described in detail herein, is the unitary disposable absorbent article, diaper 10, shown in FIG. 1. As used herein, the term "diaper" refers to an absorbent article generally worn by infants and incontinent persons about the lower torso. The present invention is also applicable to other absorbent articles such as training briefs, incontinence briefs, incontinence undergarments, absorbent inserts, diaper holders and liners, feminine hygiene garments, and the like.

FIG. 1 is a plan view of the diaper 10 of the present invention in a flat-out, state with portions of the structure being cut-away to more clearly show the construction of the diaper 10. The portion of the diaper 10 which faces the wearer is oriented towards the viewer. As shown in FIG. 1, the diaper 10 preferably comprises a liquid pervious topsheet 20; a liquid impervious backsheet 12; an absorbent core 18, which is preferably positioned between at least a portion of the topsheet 20 and the backsheet 12; side panels 30; elasticized leg cuffs 32; an elastic waist feature 34; and a fastening system generally designated 42. Diaper 10 is shown in FIG. 1 to have a first waist region 35, a second waist region 36 opposed to the first waist region 35 and a crotch region 37 located between the first waist region and the second waist region. The crotch region 37 further includes a first crotch portion 38, which is preferably in the front half of the diaper 10, and a second crotch portion 39, which is preferably in the rear half of the diaper 10. The periphery of the diaper 10 is defined by the outer edges of the diaper 10 in which the longitudinal edges 28 run generally parallel to the longitudinal centerline 100 of the diaper 10 and the end edges 29 run between the longitudiral edges 28 generally parallel to the lateral centerline 110 of the diaper 10.

The chassis 22 of the diaper 10 comprises the main body of the diaper 10. The chassis 22 comprises at least a portion of the absorbent, core 18 and preferably an outer covering layer including the topsheet 20 and the backsheet 12. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 20, the backsheet 12, and the chassis 22 may be assembled in a variety of well known configurations, preferred diaper configurations are described generally in U.S. Pat. No. 3,860, 003 entitled "Contractible Side Portions for Elisposable Diaper" which issued to Kenneth B. Buell on Jan. 14, 1975;

U.S. Pat. No. 5,151,092 issued to Buell on Sep. 9, 1992; U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; each of which is incorporated herein by reference.

In the preferred embodiment shown in the figures, the diaper, designated generally as 10, includes a liquid impervious outer sheet or backsheet 12 extending along the bottom surface of the diaper 10. The backsheet 12 has an outer or garment-facing surface 14 which faces away from the wearer and an inner or bodyfacing surface 16 which generally contacts the absorbent core 18 of the diaper 10. The backsheet 12 prevents the exudates absorbed and contained therein from soiling articles which may contact the diaper 10, such as bed sheets and undergarments. In preferred embodiments, the backsheet 12 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 10 while still preventing exudates from passing through the backsheet 12. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT application Ser. No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 12, or any portion thereof, may be elastically extensible in one or more directions. In one embodiment the backsheet 12 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 12 may comprise elastomeric films, foams, strands, or combinations of these or other suitable materials with nonwovens or synthetic films.

The backsheet 12 may be joined to the topsheet 20, the absorbent core 18 or any other element of the diaper 10 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,9869 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The topsheet 20 is preferably positioned adjacent the body-facing surface 24 of the absorbent core 18 and may be joined thereto and/or to the backsheet 12 by any attachment means known in the art. Suitable attachment means are described above with respect to means for joining the backsheet 12 to other elements of the diaper 10. In one preferred embodiment of the present invention, the topsheet 20 and the backsheet 12 are joined directly to each other in some locations and are indirectly joined together in other locations by directly joining them to other elements of the diaper 10.

The topsheet 20 is preferably compliant, soft feeling, and non-irritating to the wearer's skin. Further, at least a portion of the topsheet 20 is liquid pervious, permitting liquids to readily penetrate through its thickness. A suitable topsheet 20 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wet-laid, meltblown, hydroentangled, or otherwise processed as is known in the art. One suitable topsheet 20 comprising a web of staple length polypropylene fibers is manufactured by Veratec, Inc., a Division of International Paper Company of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 20 is made of a hydrophobic material or is treated to be hydrophobic in order to isolate the wearer's skin from liquids contained in the absorbent core 18. If the topsheet 20 is made of a hydrophobic material. preferably at least the upper surface of the topsheet 20 is treated to be hydrophilic so that liquids will transfer through the topsheet more rapidly. This diminishes the likelihood that body exudates will flow off the topsheet 20 rather than being drawn through the topsheet 20 and being absorbed by the absorbent core 18. The topsheet 20 can be rendered hydrophilic by treating it with a surfactant or by incorporating a surfactant into the topsheet. Suitable methods for treating the topsheet 20 with a surfactant include spraying the topsheet 20 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 20 may be coated with a lotion as is known in the art. Examples of suitable lotions include those described in U.S. Pat. Nos. 5,607,760 issued on Mar. 4, 1997; 5,609,587 issued on Mar. 11, 1997; 5,635,191 issued on Jun. 3, 1997; and 5,643,588 issued on Jul. 1, 1997 each of which issued to Donald C. Roe. Further, the topsheet 20, the backsheet 12 or any portion of the topsheet or backsheet may be embossed and/or matte finished to provide a more cloth like appearance.

The absorbent core 18 may comprise any absorbent material which is generally compressible, conformable, non-irritating to the wearer's skin, and capable of absorbing and retaining liquids such as urine and other certain body exudates. The absorbent core 18 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 18 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 18 should be compatible with the design loading and the intended use of the diaper 10.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; and U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article !For Low-Viscosity Fecal Material" issued to Roe on Aug. 30, 1994. Each of these patents is incorporated herein by reference.

The diaper 10 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 26 of the absorbent core 18 and generally forms at least a portion of the end edge 29 of the diaper 10. Disposable diapers are often constructed so as to have two elastic waist features, one positioned in the first waist region 35 and one positioned in the second waist region 36. Further, while the elastic waist feature 34 or any of its constituent elements may comprise one or more separate elements affixed to the diaper 10, the elastic waist feature 34 may be constructed as an extension of other elements of the diaper 10, such as the backsheet 12, the topsheet 20, or both the backsheet 12 and the topsheet 20.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992, and U.S. Pat. No. 5,221,274 issued to Buell on Jun. 22, 1993. Other suitable waist configurations may include waist-cap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 10 may also include a fastening system 42. The fastening system 42 preferably maintains the first waist region 35 and the second waist region 36 in an overlapping configuration so as to provide lateral tensions about the circumference of the diaper 10 to hold the diaper 10 on the wearer. The fastening system 42 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the diaper in a disposal configuration as disclosed in U.S. Pat. No. 4,963,140 issued to Robertson et al. on Oct. 16, 1990. Each of these patents is incorporated herein by reference. In an alternative embodiment, opposing sides of the diaper may be formed into a pant.

The diaper 10 may also comprise side panels 30. The side panels 30 may be elastic or extensible to provide a more comfortable and contouring fit by initially conformably fitting the diaper 10 to the wearer and sustaining this fit throughout the time of wear well past when the diaper 10 has been loaded with exudates since the elasticized side panels 30 allow the sides of the diaper 10 to expand and contract. The side panels 30 may also provide more effective application of the diaper 10 because even if the diaperer pulls one elasticized side panel 30 farther than the other during application, the diaper 10 will "self-adjust" during wear.

While the diaper 10 of the present invention preferably has the side panels 30 disposed in the second waist region 36, the diaper 10 may be provided with side panels 30 disposed in the first waist region 35 or in both the first waist region 35 and the second waist region 36. The side panels 30 may be constructed in any suitable configuration. Examples of diapers with elasticized side panels are disclosed in U.S. Pat. No. 4,957,067, entitled "Disposable Diaper Having Shitted Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/915,471 entitled "Absorbent Article With Multi-Directional Extensible Side Panels" filed Aug. 20, 1997 in the names of Robles, et al.; each of which is incorporated herein by reference.

The diaper 10 preferably further includes leg cuffs 32 that provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) that improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs 56 and barrier cuffs 58.

Embodiments of the present invention may also include pockets for receiving and containing waste, spacers which provide voids for waste, barriers for limiting the movement of waste in the article, compartments or voids which accept and contain waste materials deposited in the article, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" published Jul. 7, 1994 in the name of Freeland, et al.; and U.S. Pat. No. 5,653,703 entitled "Absorbent Article Having Angular Upstanding Transverse Partition," which issued Aug. 5, 1997 to Roe et al. All of the above-cited references are hereby incorporated by reference herein.

As shown in FIGS. 1–4. in the diaper 10 of the present invention, fiber optic strands 64 is provided to enable an indication of the presence or absence of waste materials to be viewed from outside the diaper 10. When the diaper 10 is soiled, the bodily wastes in proximity to the transmission end 68 of the fiber optic strands 64 block an amount of light from reaching the transmission end 68 and, thereby, block the transmission of that light to the reception end 70. Alternatively, a source of illumination in the diaper 10 may illuminate upon detecting the presence of bodily waste, and this illumination is transmitted to the reception end 70 of the fiber optic strands 64. Either of these embodiments will change the visual appearance of the reception end 70 of the fiber optic strands 64 and, thereby, will change the visual appearance of the backsheet 12 or other portion of the diaper 10 adjacent to the reception end 70 and will provide a visual indication to the caretaker that the diaper 10 has been soiled.

Figure 2:
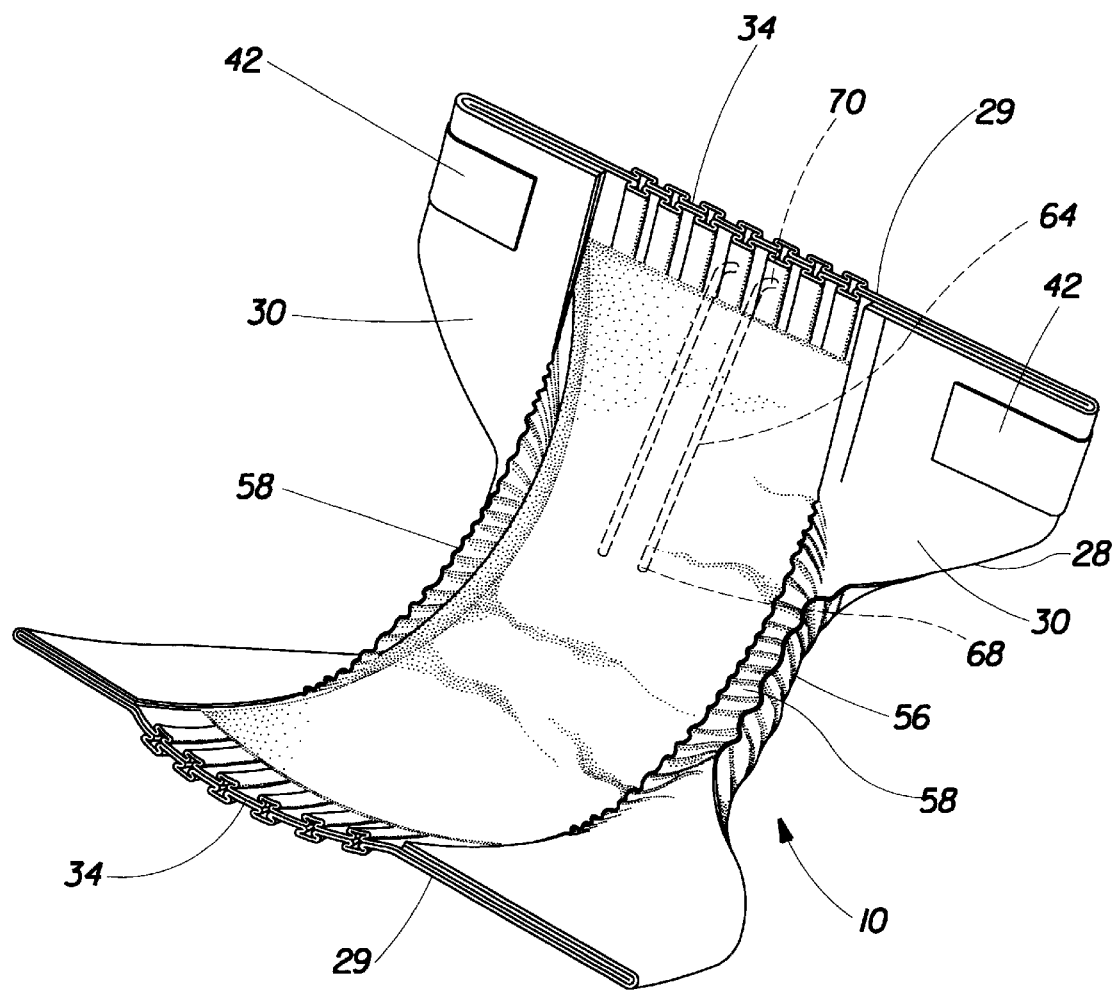
FIG. 2 is a front top perspective of the diaper of FIG. 1.
Figure 3:
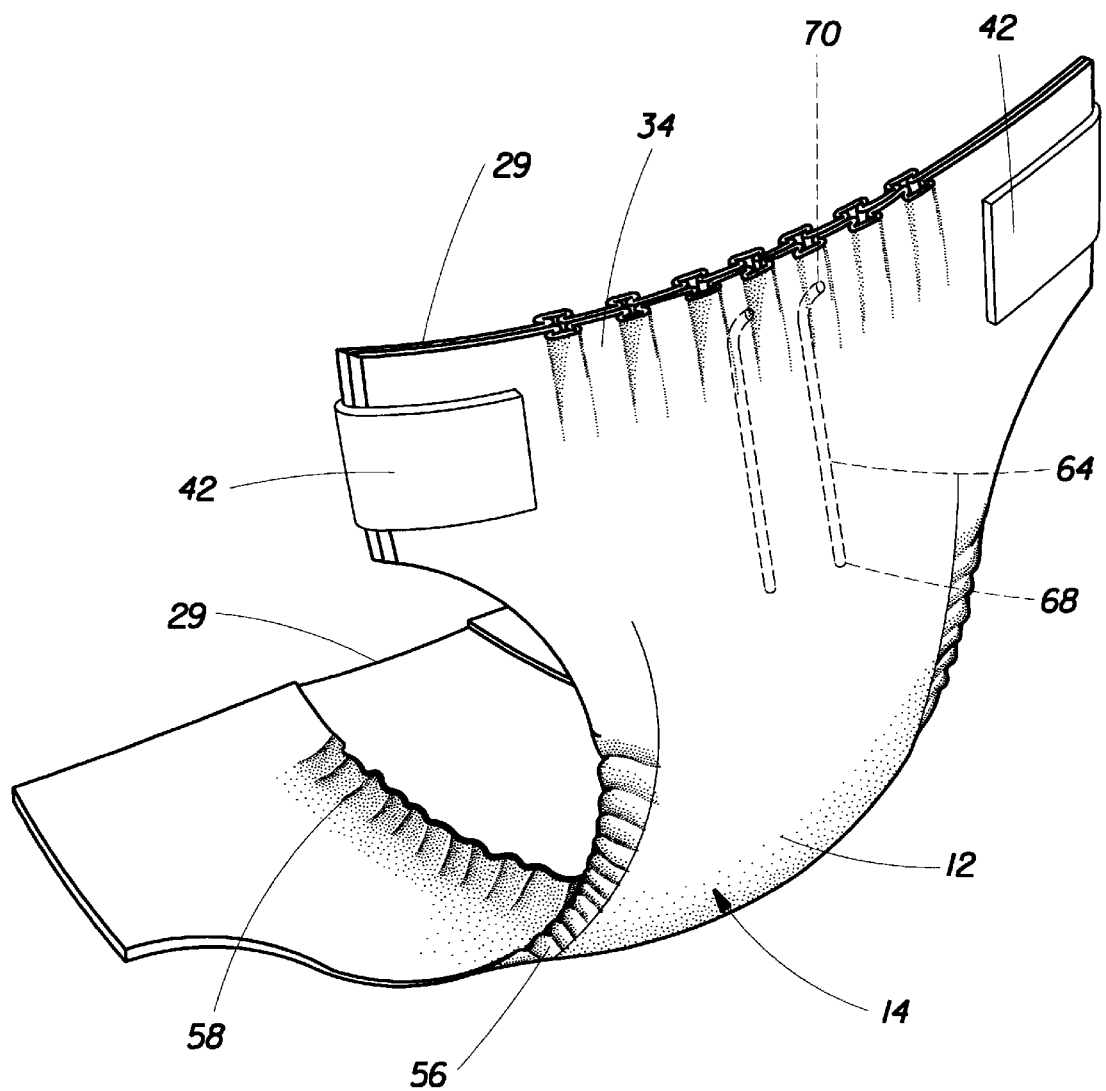
FIG. 3 is a back bottom perspective view of the diaper of FIG. 1.

In one preferred embodiment shown in FIGS. 1, 2 and 3, the fiber optic material comprises strands 64 that have a transmission end 68 disposed between the topsheet 20 and the absorbent core 18 in the rear half of diaper 10, and a reception end 70 disposed adjacent to the backsheet 12 in the second waist region 36, which is preferably the rear waist region of the diaper 10. Alternatively, the transmission end

68 of the fiber optic strand material 64 may be disposed anywhere in diaper 10 such that it would indicate the presence of waste materials deposited in diaper 10. Thus, the transmission end 68 may be integral with or disposed adjacent to the topsheet 20, an acquisition component 74, such as the macroporous acquisition component shown in FIG. 9, between topsheet 20 and absorbent core 18, registered within a hole in the absorbent core 18, such as opening 43, at the body-facing surface of the absorbent core 24, in a pocket or void, or along either a barrier leg cuff 58 or a barrier waist cuff 60. The reception end 70 of fiber optic strand material 64 may also be disposed in any location in diaper 10 such that when the diaper 10 is soiled, the reception end 70 provides a visually detectable indication that diaper 10 is soiled. The reception end 70, for example, may also be disposed adjacent to the backsheet 12 in the first waist region 35, which is preferably the front waist region, or the crotch region 37. Alternatively, the reception end 70 may extend through backsheet 12 or through a seam between the backsheet 12 and the topsheet 20 so that the reception end 70 is directly visible to the caretaker.

As shown in FIG. 10, the fiber optic strands 64 may be disposed in many configurations within the diaper 10. FIG. 10a shows an arrangement of multiple fiber optic strands 64 wherein the strands 64 are bundled in the middle, but the transmission ends 68 and the reception ends 70 of the strands 64 are loose. This arrangement allows the transmission ends 68 and the reception ends 70 to be disposed in different locations in the diaper such that bodily waste can be detected from multiple locations in the diaper and indications of the presence of bodily wastes can be visible at multiple locations of the diaper. In one variation of this embodiment, at least one fiber optic strand 64 from each of the multiple locations where the transmission ends 68 are disposed can be run to each location where reception ends 70 are disposed. This allows the caretaker to check for the presence of bodily wastes in any of several locations within the diaper 10 at the most convenient of several remote locations such as at the front or rear waist region, or along one of the longitudinal edges 28 at the leg openings of the diaper 10 so that extra articles of clothing such as pants, shorts, shirts, etc. do not have to be removed or adjusted. Additionally, the reception end 70 of one or more strands may be disposed in or on a tab member that extends from the diaper and may be extended outside the clothing of the wearer to provide an easy and convenient location to check for the presence or absence of bodily waste in the diaper 10.

Figure 10A:
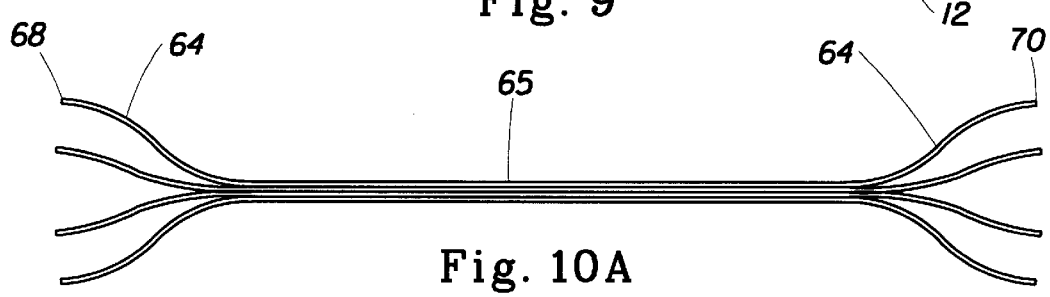
FIGS. 10a through 10e are schematic views of various alternative dispositions of fiber optic strands for the present invention.
Figure 10B:
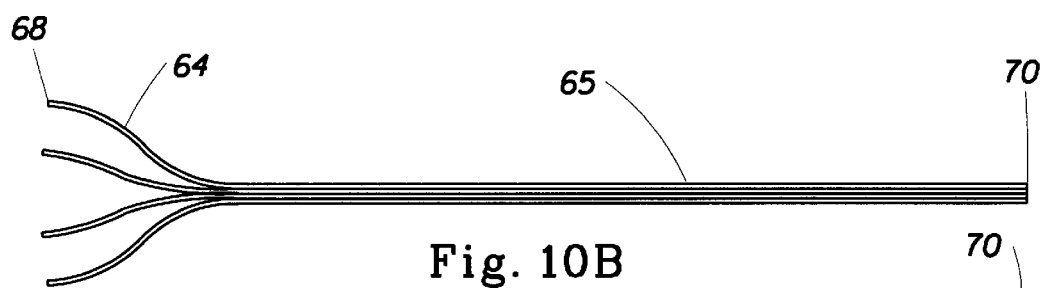
Figure 10C:
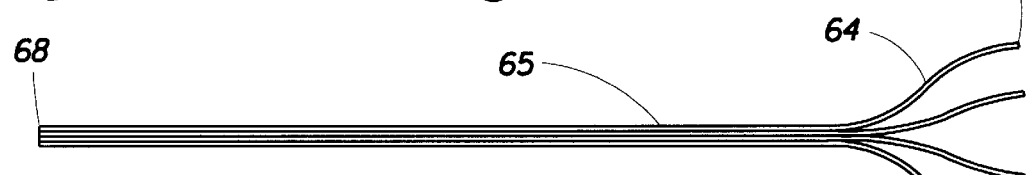
Figure 10D:
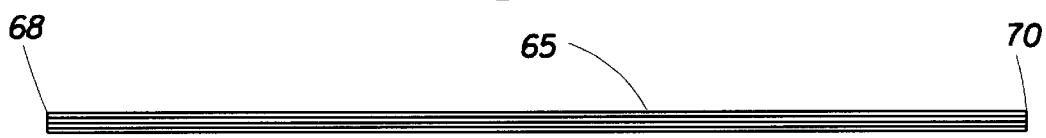
Figure 10E:
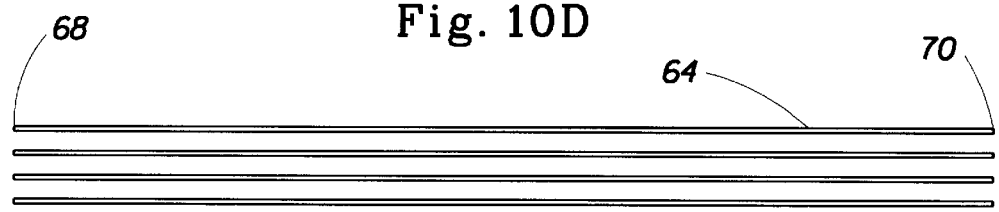

Alternatively. FIGS. 10b and 10c show embodiments wherein either the transmission ends 68 or the reception ends 70, respectively, are loose and the remaining portions of the fiber optic strands are bundled together. This allows either the presence of bodily waste in any one or more location of the diaper 10 to provide an indication at one remote location of the diaper 10, or the presence of bodily waste at one location of the diaper 10 to provide an indication at a multiple number of remote locations of the diaper 10. FIG. 10d shows that a bundle 65 of fiber optic strands can be disposed in the diaper 10 such that the presence or absence of bodily waste at the location where the transmission end 68 of the bundle 65 is disposed can be indicated at the remote location where the reception end 70 of the bundle 65 of the fiber optic strands 64 is disposed. In yet another embodiment shown in FIG. 10e, individual fiber optic strands 64 (or individual bundles 65 of fiber optic strands) can be disposed in multiple locations of the diaper 10. In this embodiment, the presence or absence of bodily waste in different locations of the diaper 10 can be indicated at different locations (or the same location if the reception ends 70 of each fiber optic strand 64 or bundle 65 is disposed in the same location of the diaper 10) of the diaper 10 where each of the reception ends 70 of fiber optic strands 64 or bundles 65 are disposed.

In an alternative embodiment such as the one shown in FIGS. 4–8, the fiber optic strands 64 may be fixed in a matrix 72 disposed in the diaper 10. For example, the matrix may comprise two or more fiber optic strands 64 braided together to provide strength to the individual strands 64. Alternatively, the matrix may comprise two or more fiber optic strands 64, whether braided or not, and one or more materials that would support the strands in the matrix. A woven or nonwoven material. tissue, paper, plastic film, polymer, adhesive or tape, for example, could be used to at least partially encompass or circumscribe the matrix. Filler material such as a woven material. a nonwoven material. a polymer, an adhesive such as a glue, cellulose fibers, air felt, etc. could be interspersed between and/or among the strands 64 of the matrix 72. A block 66 or sheet 67 of material such as a plastic film, an adhesive such as a glue, polymer such as a thermosetting resin or a polyolefin, or a woven or nonwoven material may at least partially encompass or circumscribe the matrix 72 as well as be interspersed between and/or among the individual strands 64.

Figure 4:
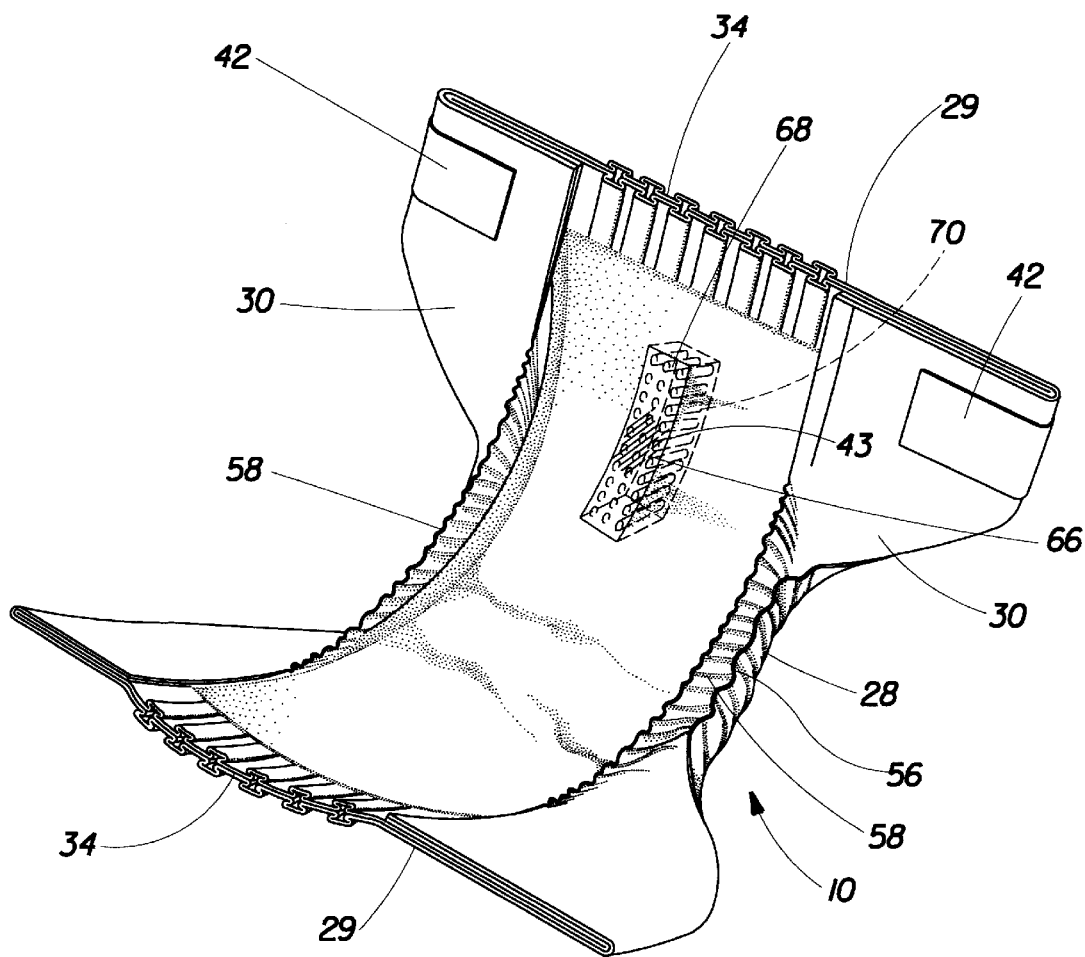
FIG. 4 is a front top perspective view of an alternative embodiment of an article of the present invention wherein the article is a diaper.
Figure 5:
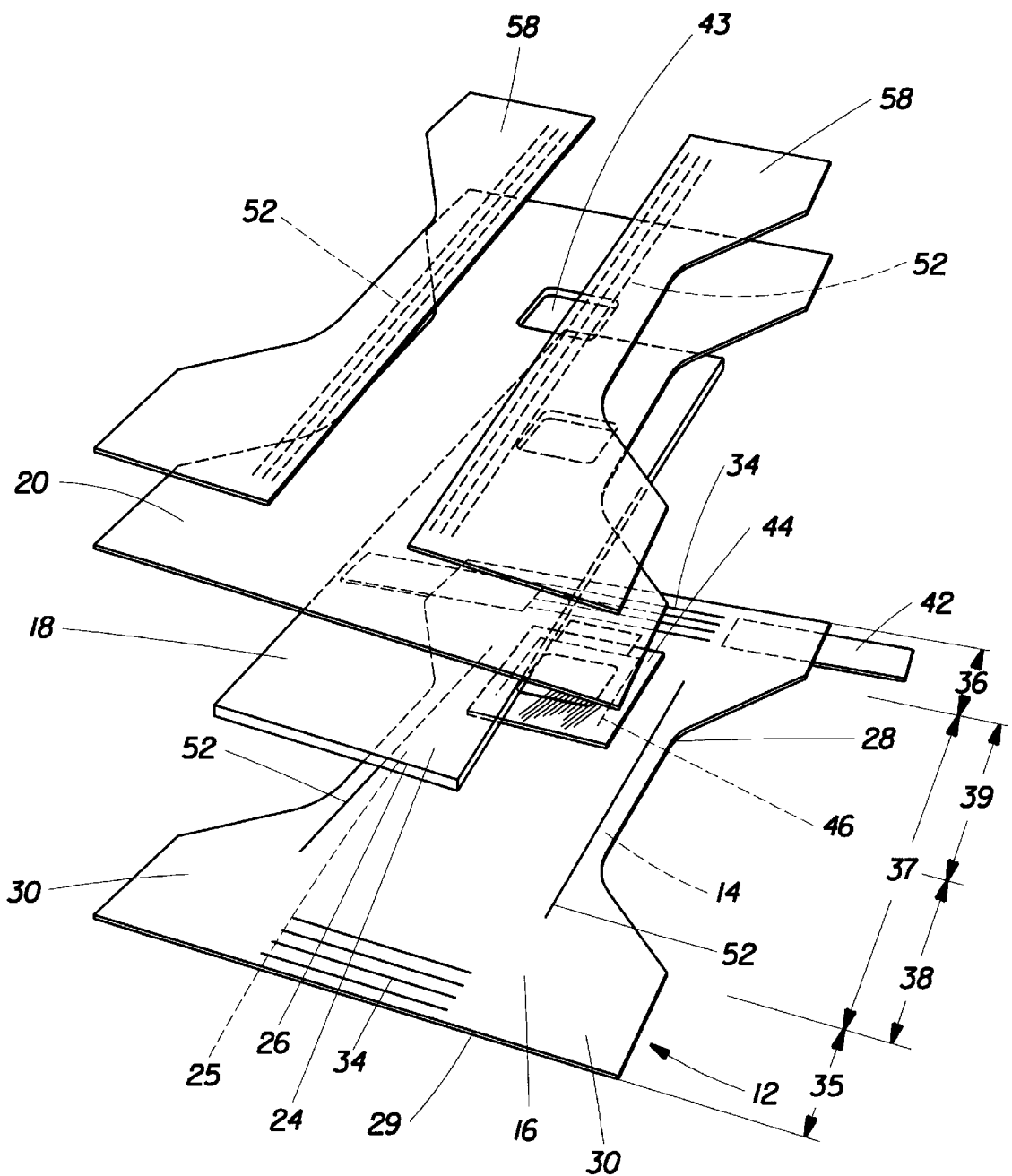
FIG. 5 is a partially exploded view of the diaper of FIG. 4.
Figure 6:
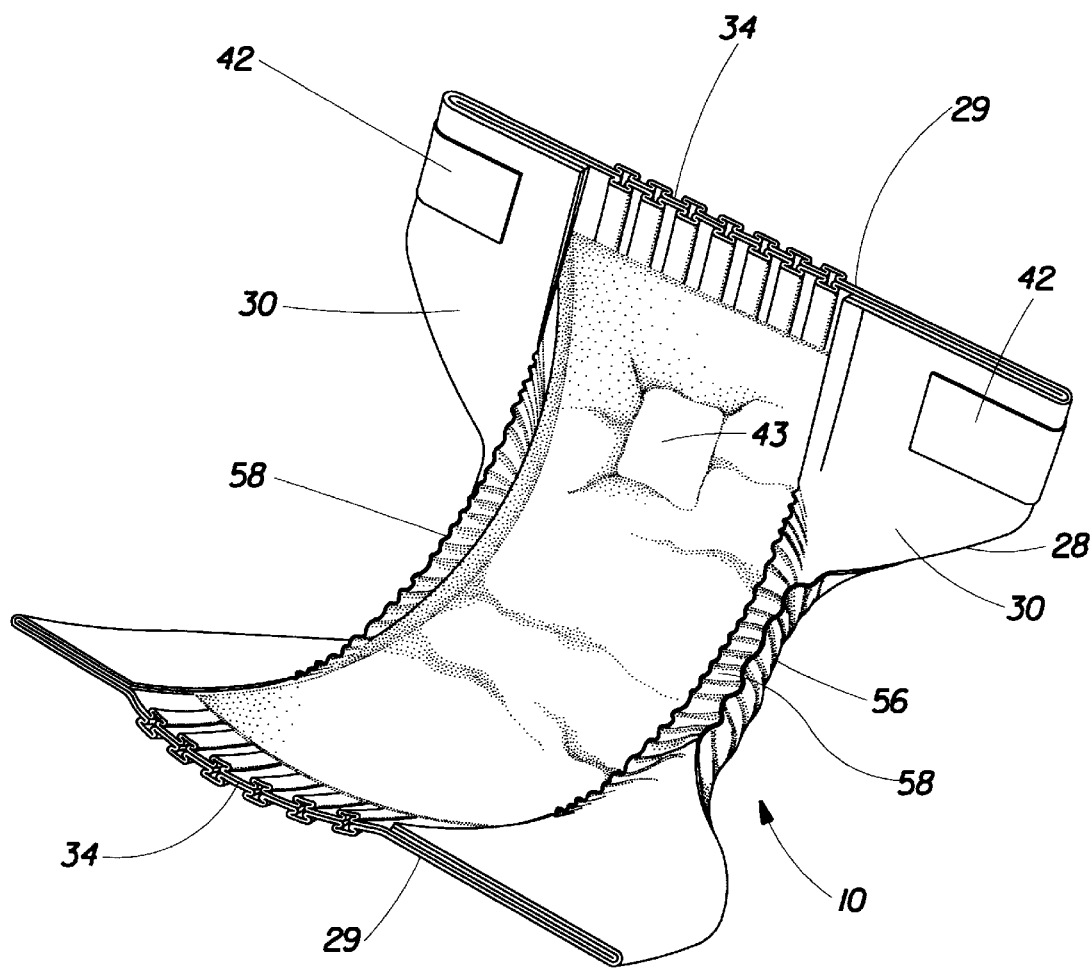
FIG. 6 is a front top perspective view of the diaper made in accordance with the embodiment of the present invention shown in FIG. 4.
Figure 7:
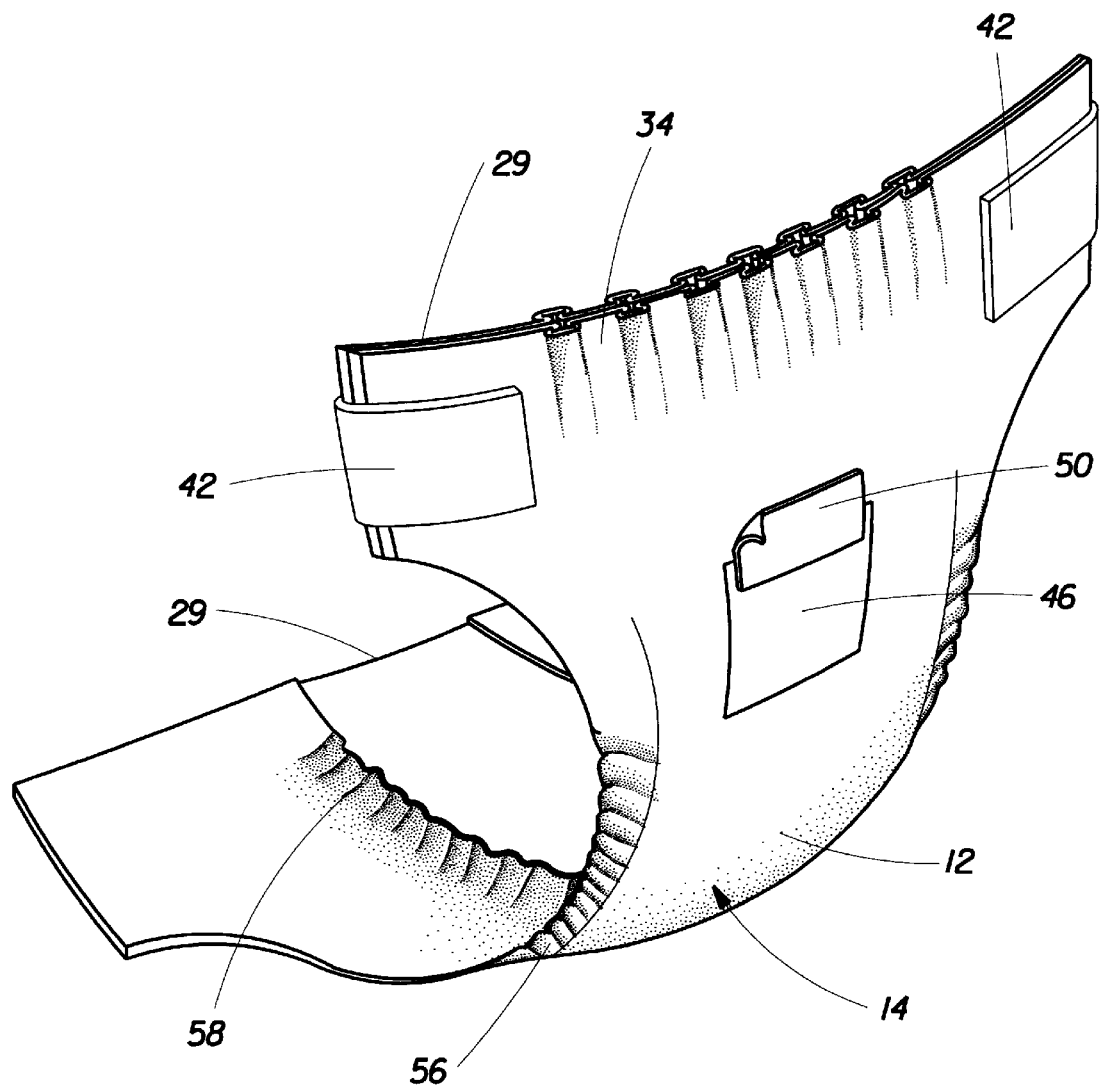
FIG. 7 is a back bottom perspective view of the diaper of FIG. 4 depicting the inspection porthole in a first, covered position.
Figure 8:
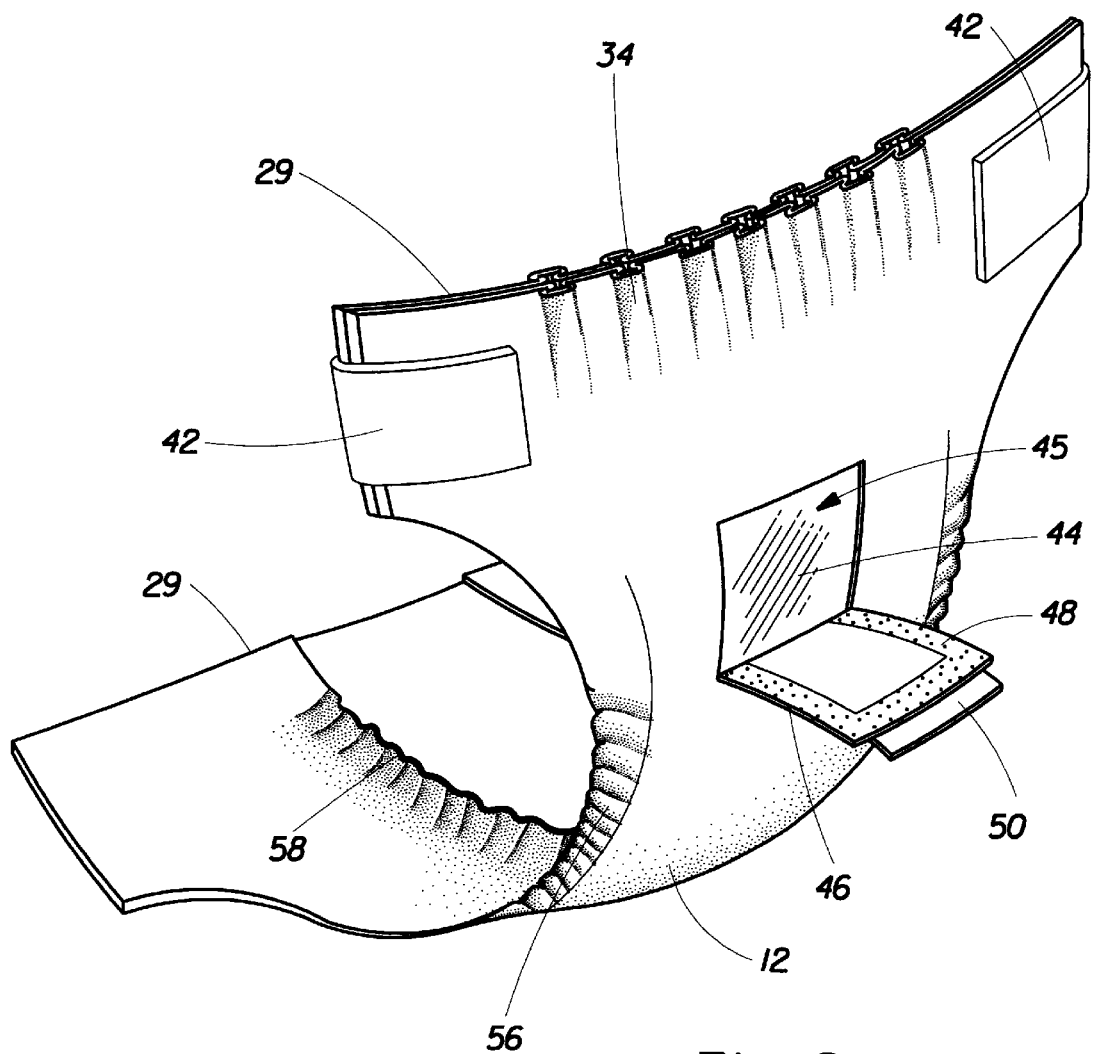
FIG. 8 is a back bottom perspective view of the diaper of FIG. 4 depicting the inspection porthole in a second open or inspection position.
Figure 9:
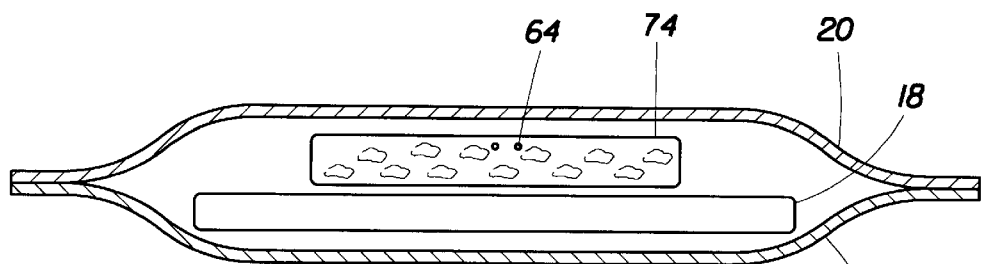
FIG. 9 is a cross-section view of an alternative embodiment of an article of the present invention, wherein the article is a diaper.

In one particular embodiment, the fiber optic strands 64 may be fixed in a matrix 72 within a block 66 or sheet 67 and disposed in an opening 43 formed in at least the absorbent core 18 as shown in FIG. 4. The block 66 or sheet 67 supports the fiber optic strands 64 in the opening 43. However, any of the other materials or orientations described above may be used to support the fiber optic strands 64 in opening 43. Alternatively, a matrix of individual fiber optic strands 64 may be disposed in the opening 43 of the absorbent core and supported by the resiliency of the absorbent core surrounding the opening 43. In any of these embodiments, the opening 43 is preferably located in the rear half of the diaper 10, with the position of the opening 43 being selected so as to coincide with the portion of the diaper 10 where waste materials are most commonly deposited. The opening 43 may also extend through the topsheet 20 and/or backsheet 12. In the representative embodiment shown in FIGS. 4–8, for example, the opening 43 extends through the topsheet 20, absorbent core 18 and backsheet 12, is substantially rectangular, and is approximately 1 inch by 1.5 inches in dimension. However, it is to be understood that the size and shape of the opening 43 and matrix 72 of fiber optic strands 64 may vary depending upon the type and intended use of the diaper, without departing from the scope of the invention. In this embodiment, the transmission end 68 of the matrix 72 of fiber optic strands 64 extends through topsheet 20 into the interior of diaper 10. The transmission end 68, however, may be disposed in any location where it will indicate the presence of waste materials deposited in diaper 10. Thus, the transmission end 68 may be located in areas such as disposed between the topsheet 20 and absorbent core 18, extending into or through an acquisition component 74, disposed between absorbent core 18 and an acquisition component 74, disposed in a pocket or void, or registered in an opening 43 at the body-facing surface of the absorbent core 24. When the transmission end 68 of the matrix 72 of fiber optic strands 64 contacts, is adjacent to or is in the vicinity of the waste material deposited in diaper 10, the change in the reception end 70 of the matrix 72 of fiber optic strands 64, which is disposed adjacent to backsheet 12, indicates the presence of waste materials and is visible through backsheet 12.

In a further aspect of the invention, opening 43 may extend through backsheet 12 to provide a more direct view of the reception end 70 of the matrix 72 of fiber optic strand material 64 than would be visible through backsheet 12. In this embodiment shown in FIGS. 4–7, a liquid impermeable transparent or translucent overlay 44 is positioned across the opening 43, in order to seal the opening and prevent body fluids and other waste materials from leaking through the inspection port 45. In the representative embodiment shown in the figures, the overlay 44 is positioned between the bottom surface of the core 18 and the upper surface 16 of the backsheet 12. In this position, the overlay 44 is sealed to the top surface of the backsheet 12 by any suitable means, such as thermal welding or adhesives, so that a fluid-tight seal is formed between the backsheet and overlay to prevent fluid leakage. While the overlay 44 has been described as being attached between the core 18 and backsheet 12, it is to be understood that the overlay could also be attached on the outer surface 14 of the backsheet 12 without departing from the scope of the invention.

In order to hide the opening 43, overlay 44, and inspection port 45 between inspection viewings of the diaper contents, a concealing structure may be provided on the outer surface 14 of the backsheet 12. In the embodiment shown in the figures, the concealing structure is a releasable, reclosable cover 46 which extends across the overlay 44. By "releasable", it is meant that at least a part of cover 46 can be selectively peeled back or disconnected from diaper 10 to reveal inspection port 45 for viewing the interior of the diaper in a non-intrusive and convenient manner. The cover 46 is shown in a closed, attached position against the backsheet 12 of the diaper 10 in FIG. 7, and in an open, detached position in FIG. 8. The cover 46 is securely attached (e.g. in a hingeable fashion) along one portion to the outer surface 14 of the backsheet 12 to prevent the cover 46 from separating from the diaper 10. An adhesive material 48 is preferably provided on the side of the cover 46 facing the backsheet 12 to enable the cover to adhere to the overlay 44, or the surface of the backsheet 12 surrounding the overlay. Preferably, the adhesive material applied to the cover 46 remains sticky after detachment to enable the cover to be detached and reattached to the overlay 44 multiple times as needed. Alternatively, any suitable mechanical fastener, such as a hook and loop fastener, or electrical fastener, such as electrets (e.g., electrostatic attraction), may be used to releasably and reclosably secure the cover 46 to the backsheet 12 or the overlay 44 either by affixing the fastener directly to the cover 46 and the overlay 44, or to the tab 50 and/or the outer surface 14 of the backsheet 12 adjacent to the inspection port 45.

In a preferred embodiment an adhesive 48 is applied around the peripheral edges of the cover, as shown in FIG. 4, to enable the cover to be more easily detached from the overlay 44. The cover 46 is preferably comprised of a pliable, non-transparent material. such as a flexible plastic. The cover 46 is preferably pliable to allow the cover to easily conform to shifts in the position of the diaper as the wearer moves, and to prevent the cover 46 from inadvertently poking the wearer and causing discomfort. The cover 46 may be integrally formed with the outer sheet 12 by cutting the outer sheet and peeling the cut portion back to form the cover. Alternatively, the cover 46 may be a separate piece of material. having the same or different characteristics from the backsheet 12, which is thermally welded or attached by some other permanent means, along one edge to the backsheet 12.

To assist in detaching the cover 46 from the backsheet 12, a detaching mechanism, such as a tab 50, may be provided on the cover. The tab 50 extends from at least one edge of the cover 46, beyond the adhesive 48, to provide a loose portion which can be easily grasped to lift the cover away from the overlay.

In yet another preferred embodiment, diaper 10 may further comprise an auxiliary light source that will provide additional illumination inside the diaper 10. Such a light source will provide a clearer signal to be displayed at the reception end 70 of fiber optic strands 64 or bundles 65. This will, in turn, provide a more definite indication when bodily wastes are present in the diaper 10. Any form of illumination can be incorporated into the diaper. For example, a battery and a light bulb, such as a watch light bulb, or a piezoelectric element could be disposed in a portion of the diaper 10 such as between the topsheet 20 and the absorbent core 18, in an acquisition component 74, in the absorbent core 18, between the absorbent core 18 and the backsheet 12, etc. In one embodiment, the caretaker could turn on the light source when putting the diaper 10 on the wearer. In an alternative embodiment, the light bulb or piezoelectric element could be part of a circuit that is completed by urine or other bodily waste eletrically connecting two elements of the circuit. Examples of such a circuit are shown in U.S. Pat. No. 2,127,538 entitled "Signaling Device" issued to Harry W. Seiger on Aug. 3, 1938 and U.S. Pat. No. 4,796,014 entitled "Device For Detecting Urine In Diapers" issued to Jack T. Chia on Jan. 3, 1989, each of which is hereby incorporated by reference.

Alternatively, a material that provides biologically or chemically produced luminescence could be disposed in the diaper 10. Luciferin, for example, is a biologically luminescent material that illuminates when undergoing oxidation promoted by the catalyst luciferase. In one embodiment, the bioluminescent or chemical luminescent material could be provided in the diaper with a catalyst in a capsule that can be broken by the caretaker bending or pinching the capsule when putting the diaper on the wearer to illuminate the material. In an alternative embodiment, a vial. or micro or nanocapsules could be activated, opened, or soluble in the presence of exudates, and would thus illuminate when the diaper was soiled. For example the vial or capsules could be activated, opened or soluble in the presence of fecal enzymes, certain pH ranges, ammonia, water or may react with other components of feces and/or urine such as carbohydrates, etc. Alternatively, the luminescent material itself may be activated by fecal enzymes, certain pH ranges, ammonia, water or may react with other components of feces and/or urine such as carbohydrates, etc.

The diaper 10 embodiment of the present invention may be applied to a wearer by positioning one of the waist regions, preferably the second waist region 36, under the wearer's back and drawing the remainder of the diaper 10 between the wearer's legs. The other waist region, preferably the first waist region 35, is positioned across the front of the wearer. The diaperer then wraps the side panels 30 around the wearer such that the first waist region 35 and the second waist region 36 are in an overlapping configuration. The side panels 30 will typically be extended and tensioned during this operation so as to conform to the size and shape of the wearer. The fastening system 42 is secured to effect a side closure.

The foregoing description of preferred embodiments of the invention has been presented for purposes of illustration and description. It is not intended to be exhaustive or to limit the invention to the precise form disclosed. Obvious modifications or variations are possible in light of the above teachings.

What is claimed is:

1. An absorbent article having a first waist region, a second waist region and a crotch region comprising:
   (a) a liquid permeable topsheet;
   (b) a backsheet joined with said topsheet;
   (c) an absorbent core having a body-facing surface and a garment-facing surface located between at least a portion of said top sheet and said backsheet; and
   (d) a fiber optic strand having two ends, said first end disposed in said crotch region and said second end disposed in said absorbent article such that said second end provides an indication that is visible from outside of said absorbent article when said absorbent article has been soiled.

2. The absorbent article of claim 1, wherein said second end is disposed adjacent to said backsheet.

3. The absorbent article of claim 1, wherein said second end is disposed adjacent to an opening in said backsheet.

4. The absorbent article of claim 1, wherein said second end is disposed in a waist region.

5. The absorbent article of claim 1, wherein said second end is disposed through a seam joining said topsheet and said backsheet along the periphery of the absorbent article.

6. The absorbent article of claim 5, wherein said seam is located in a waist region.

7. The absorbent article of claim 5, further comprising a longitudinal edge wherein said seam is located at said longitudinal edge.

8. The absorbent article of claim 1, wherein said second end is disposed in a tab extending outwardly from said absorbent article.

9. The absorbent article of claim 1, wherein said first end is disposed on said topsheet.

10. The absorbent article of claim 1, wherein said first end is disposed between said topsheet and said absorbent core.

11. The absorbent article of claim 1, wherein said first end is integral with said topsheet.

12. The absorbent article of claim 1, further comprising an acquisition component disposed adjacent to said body-facing surface of said absorbent core wherein said first end of said fiber optic strand is disposed in said acquisition component.

13. The absorbent article of claim 1, further comprising a source of illumination.

14. The absorbent article of claim 13, wherein said source of illumination is selected from the group consisting of a light bulb, a piezoelectric element, a chemically produced luminescence, a biologically produced luminescence.

15. The absorbent article of claim 13, wherein said source of illumination comprises a capsule containing a catalyst and a luminescent material.

16. The absorbent article of claim 15, wherein said source of illumination is capable of illumination when said capsule frees said catalyst in response to said capsule contacting feces or urine.

17. The absorbent article of claim 13, wherein said source of illumination comprises a luminescent material and is capable of illumination when said luminescent material contacts feces or urine.

18. An absorbent article having, a first waist region, a second waist region and a crotch region comprising:
   (a) a liquid permeable topsheet;
   (b) a backsheet joined with said topsheet;
   (c) an absorbent core located between at least a portion of said topsheet and said backsheet; and
   (d) a fiber optic strand having two ends, said first end disposed in said crotch region and said second end disposed adjacent to an opening in said backsheet.

19. The absorbent article of claim 18, wherein said opening in said backsheet is covered with a translucent material.

20. The absorbent article of claim 19, wherein said translucent material is a material selected from the group consisting of a nonwoven material, a plastic film, and laminates thereof.

21. The absorbent article of claim 18, wherein said opening in said backsheet is covered with a transparent material.

22. The absorbent article of claim 21, wherein said transparent material is a plastic film.

23. The absorbent article of claim 18, wherein said second end of said fiber optic strand is disposed in said opening of said backsheet.

24. The absorbent article of claim 18, further comprising a second fiber optic strand, wherein said first and said second fiber optic strands are disposed in a matrix.

25. The absorbent article of claim 24, wherein said matrix further comprises at least one material selected from the group consisting of a nonwoven material, a woven material, a polymer, an adhesive, and cellulose fibers.

26. The absorbent article of claim 24, wherein said matrix is disposed in an opening of said absorbent core.

27. An absorbent article having a first waist region, a second waist region and a crotch region comprising:
   (a) a liquid permeable topsheet;
   (b) a backsheet joined with said topsheet;
   (c) an absorbent core having a body-facing surface and a garment-facing surface located between at least a portion of said topsheet and said backsheet;
   (d) a first fiber optic strand having two ends, said first end disposed in said crotch region and said second end disposed in said absorbent article such that said second end provides an indication that is visible from outside of said absorbent article when said absorbent article has been soiled; and
   (e) a second fiber optic strand having, two ends said first end disposed in said crotch region and said second end disposed in said absorbent article such that said second end provides an indication that is visible from outside of said absorbent article when said absorbent article has been soiled.

28. The absorbent article of claim 27, wherein at least a portion of said first and said second fiber optic strands are bundled together.

29. The absorbent article of claim 28, wherein said first ends of said first and said second fiber optic strands are disposed separate from each other in said crotch region.

30. The absorbent article of claim 28, wherein said second ends of said first and said second fiber optic strands are disposed separate from each other such that said indication at said second end of said first fiber optic strand and said indication at said second end of said second fiber optic strand are visible at different locations from outside of said absorbent article.

31. The absorbent article of claim 28, further comprising a source of illumination.

32. The absorbent article of claim 27, wherein said first and said second fiber optic strands are disposed in a matrix.

33. The absorbent article of claim 32, wherein said matrix further comprises at least one material selected from the group consisting of a nonwoven material, a woven material, a polymer, an adhesive, and cellulose fibers.

34. The absorbent article of claim 32, wherein said matrix is disposed in an opening of said absorbent core.

35. The absorbent article of claim 32, wherein said crotch reunion has a first portion and a second portion, and said matrix is disposed in said second portion of said crotch region.

36. The absorbent article of claim 32, further comprising a source of illumination.

\* \* \* \* \*

UNITED STATES PATENT AND TRADEMARK OFFICE
CERTIFICATE OF CORRECTION

PATENT NO.   : 6,066,774
DATED        : May 23, 2000
INVENTOR(S)  : Donald C. Roe Page 1 of 1

It is certified that error appears in the above-identified patent and that said Letters Patent is hereby corrected as shown below:

Column 4,
Line 45, "longitudiral" should read -- longitudinal --.
Line 66, "Elisposable" should read -- Disposable --.

Column 6,
Line 23, "4,573,9869" should read -- 4,573,986 --.

Column 9,
Line 45, "Shitted" should read -- Shirred --.

Column 12,
Line 33, "Altematively" should read -- Alternatively --.

Signed and Sealed this

Sixteenth Day of October, 2001

Attest:

NICHOLAS P. GODICI
Attesting Officer    Acting Director of the United States Patent and Trademark Office